(12) United States Patent
Moreno Gonzalez

(10) Patent No.: US 10,350,247 B2
(45) Date of Patent: Jul. 16, 2019

(54) PHARMACEUTICAL COMPOSITION FOR PREVENTING, TREATING, AND CURING PSORIASIS INCLUDING SNAIL SLIME, CHAMOMILE, AND HONEY

(71) Applicant: MUCIDERM S.A., Santiago (CL)

(72) Inventor: Elmo Moreno Gonzalez, Santiago (CL)

(73) Assignee: MUCIDERM S.A., Santiago (CL)

( * ) Notice: Subject to any disclaimer, the term of this patent is extended or adjusted under 35 U.S.C. 154(b) by 8 days.

(21) Appl. No.: 15/501,129

(22) PCT Filed: Sep. 12, 2014

(86) PCT No.: PCT/CL2014/000046
§ 371 (c)(1),
(2) Date: Feb. 1, 2017

(87) PCT Pub. No.: WO2016/029328
PCT Pub. Date: Mar. 3, 2016

(65) Prior Publication Data
US 2017/0216368 A1 Aug. 3, 2017

(30) Foreign Application Priority Data
Aug. 25, 2014 (CL) .................... 2248-2014

(51) Int. Cl.
| A61K 35/618 | (2015.01) |
| A61K 36/28 | (2006.01) |
| A61K 9/00 | (2006.01) |
| A61K 9/06 | (2006.01) |
| A61K 35/64 | (2015.01) |
| A61K 36/185 | (2006.01) |
| A61K 35/644 | (2015.01) |

(52) U.S. Cl.
CPC .......... *A61K 35/618* (2013.01); *A61K 9/0014* (2013.01); *A61K 9/06* (2013.01); *A61K 35/64* (2013.01); *A61K 36/185* (2013.01); *A61K 36/28* (2013.01); *A61K 35/644* (2013.01); *A61K 2300/00* (2013.01)

(58) Field of Classification Search
None
See application file for complete search history.

(56) References Cited

U.S. PATENT DOCUMENTS

2010/0233111 A1* 9/2010 Wang ................ A61K 8/73
424/62
2013/0309296 A1 11/2013 Moreno Gonzalez et al.

FOREIGN PATENT DOCUMENTS

| DE | 19615293 A1 * | 10/1997 | ............. A61K 35/36 |
| ES | 2009471 A6 | 9/1989 | |
| ES | 2443816 A1 | 2/2014 | |
| WO | 9215276 A2 | 9/1992 | |
| WO | 0166079 A1 | 9/2001 | |
| WO | 2009002982 A2 | 12/2008 | |

OTHER PUBLICATIONS

Dimosthenis Tsoutsos, Despoina Kakagia & Konstantinos Tamparopoulos, The efficacy of Helix aspersa Müller extract in the healing of partial thickness burns: A novel treatment for open burn management protocols, Journal of Dermatological Treatment, 2009, pp. 219-222, vol. 20, No. 4.

A. Brieva, N. Philips, R. Tejedor, A. Guerrero, J.P. Pivel, J.L. Alonso-Lebrero, S. Gonzalez, Molecular Basis for the Regenerative Properties of a Secretion of the Mollusk Cryptomphalus aspersa, Skin Pharmacology and Physiology, 2008, pp. 15-22, vol. 21, No. 1.

The International Searching Authority, Notification of Transmittal of the International Search Report and the Written Opinion of the International Searching Authority or the Declaration, Apr. 23, 2015.

* cited by examiner

Primary Examiner — Qiuwen Mi
(74) Attorney, Agent, or Firm — Gottlieb, Rackman & Reisman, P.C.

(57) ABSTRACT

The invention relates to a pharmaceutical composition consisting of snail slime of *Helix aspersa* muller (*Cryptophalus aspersus*) (5% to 50%), chamomile extract (5% to 10%), honey (5% to 10%), and additives and/or pharmaceutically accepted excipients to form a formulation having low, intermediate or high viscosity (1 to 1000 Pa·s). By dipping a patch or bandage of gauzy fabric into the composition in the form of a lotion, shampoo, soap, cream or gel, the composition is applied on lesions caused by psoriasis. The composition can also contain natural extracts, such as marigold extract, propolis, and vegetable oils. The invention also claims a method for obtaining the composition and the use thereof to prepare a drug or device for preventing, treating or curing psoriasis lesions on the head, the skin of the body or of the face.

8 Claims, 3 Drawing Sheets a)

b)

c)

d)

PHARMACEUTICAL COMPOSITION FOR PREVENTING, TREATING, AND CURING PSORIASIS INCLUDING SNAIL SLIME, CHAMOMILE, AND HONEY

The present application is submitted as a National Phase filing of PCT/CL2014/000046 filed on Sep. 12, 2014 and now pending, which claims priority to Chile Patent Application 2248-2014 filed on Aug. 25, 2014 and now pending.

DISCUSSION OF PRIOR ART

Psoriasis is a common chronic inflammatory skin disease with basis in the etiology of environmental and genetic factors. It affects 2% of the population in ranges from mild to severe. The age of onset of psoriasis follows a bimodal distribution (between the ages 20 and 30, and 50-60 years) (Turchin et al., 2006).

About 35% of patients with psoriasis have a family history of the disease. Several environmental factors can trigger such a disease in susceptible people: infection (streptococcus, most common infection), traumatism in the skin (Koebner's phenomenon), reaction to drugs (e.g., lithium, beta blockers, malaria drugs, Inflammatory drugs, nonsteroidal anti-inflammatory drugs and glucocorticoids), and stress.

The clinical presentation of psoriasis varies depending on the morphological subclass. Plaque is the most common subtype and is usually concentrated on extension surfaces (elbows, knees and lumbar), scalp, genital areas, palms, sole, joints and nails (Turchin et al., 2006). Therapy varies depending on the severity of the disease and the degree of involvement of body surface area. However, the majority of patients (approximately 80-90%) present a relatively mild disease and the disease only has limited involvement of the skin, which can be well controlled with topical treatment.

Etiology

The cause of psoriasis is an abnormally high rate of mitosis in epidermal cells that can be related to a substance transported in the blood, a defect in the immune system. It has also been associated with a multifactorial inheritance pattern for psoriasis, which implies that both the genetic and environmental components are responsible for the manifestation of the disease. There are studies that refer to possible viral causes, immunological aspects and lipid metabolism associated with the development of the disease (Farber, 1971).

The epidermal differentiation complex gene cluster is on chromosome region 1q21.3, where the PSORS4 locus was mapped. A common deletion of two LCE genes (LCE3C_LCE3B-del) is associated with psoriasis. Individuals homozygous for the deletion have an impaired response of the skin barrier to exogenous agents, facilitating the systemic skin inflammation characteristic of psoriasis (Coto et al., 2011).

Factors that Trigger Psoriasis

1. Psychological stress: In 40% of patients, psoriasis seems to aggravate after a stressful event. If psychological problems are deteriorating the quality of life, a psychological intervention may be indicated (Gupta et al., 1989).

2. Focal infections: Focal infections are most frequently related to psoriasis, also infections of the upper respiratory tract, but sometimes dental abscess, cholecystitis or urinary tract infections cause a worsening of the disease. Proper treatment of these infections often results in a considerable improvement in the skin condition.

3. Medications: Some medications have to be avoided because they can aggravate psoriasis. This has been demonstrated for β-blockers, antimalarials, lithium carbonate, angiotensin-converting enzyme inhibitors, non-steroidal anti-inflammatory drugs and systemic corticosteroids (rebound after discontinuation of systemic treatment) (Tsankov N et al., 2000).

4. Lifestyles: It has been suggested that lifestyles are involved in the expression of psoriasis. Thus, it has been suggested that smoking and alcohol consumption aggravate the disease. It is possible that smoking and alcohol consumption are the result of psychological distress, making them responsible for the aggravation of the disease. From the practical point of view, it is important that patients improve their unhealthy lifestyles to prevent future comorbidities (Hayes and Koo, 2010).

Quality of Life

Psoriasis has a great impact on the quality of life of patients. Epidemiological studies have documented this statement. The use of questionnaires for the general Short Form 36 health survey, focusing on physical and mental status, shows that the quality of life of patients with psoriasis is affected to the same extent as patients with chronic diabetes, pulmonary diseases, infarction of infection, hypertension and malignant diseases (Rapp et al., 1999).

It is of great importance to reconcile the problems with the quality of life to take a good selection of the treatment. A discrepancy between objective score and deterioration in quality of life can sometimes be appreciated for various reasons. For example, a patient with psoriasis on a single finger has a poor quality of life score but may be barred from functioning properly at work. On the other hand, if you have a major psychological problem, you can project on the psychological impact of the disease, it is recommended that the patient follow the psychotherapy previously rather than being treated with biological products. It is important to be able to estimate the real need of a patient with psoriasis, thus justifying treatment selection (De Korke et al., 2002).

Treatments

The expression of psoriasis is very variable and may even vary within a single patient. This measure does not only cover lesions, severity, in terms of induration, erythema and desquamation or visibility of the lesions, but above all the responsiveness to anti-psoriasis treatments. Hence, management of psoriasis must reconcile with the variability of response to treatment, which to some extent may be genetically determined, but may also be the result of non-genetic factors, triggers and adaptation to treatments (Van De Kerkhof, 2008).

Patients with psoriasis have a chronic need for many years. Two strategies have to be reconciled, for the short term induction of remission and for the long term manage disease control with safety.

Vitamin D3 analogues, retinoids, tazarotene, betamethasone products, calcipotriol, topical corticosteroids and dipropionate can be said to be the first option in view of their safety. In many patients, however, these treatments should be combined with a topical corticosteroid resistance medium to improve efficacy. In some patients, depending on the treatment history, a topical corticosteroid of a higher level may be necessary. If maintenance treatment with analog vitamin D3 or topical retinoids is not effective enough, corticosteroids are not suitable as a maintenance treatment. (Van de Kerkhof, 2008).

Anti-psoriatics of classic use include methotrexate, cyclosporine, fumarates and acitretin. The selection among these systemic agents is based mainly on the existence of co-morbidities in the patient and the results of the previous treatment. Cyclosporine is not suitable as a maintenance treatment. Methotrexate is the first option in case of severe disease, and fumarates or acitretin are more indicated in moderate disease (Van de Kerkhof, 2008).

Topical Treatments

Topical therapy is the cornerstone of treatment in the management of psoriasis. It plays an important role as monotherapy in mild to moderate psoriasis, and is mainly used as adjuvant treatment in moderate to severe forms of the disease.

Over the past decade, topical treatment of psoriasis has evolved from ancient applications, such as coal tar to aesthetically more acceptable and effective options containing topical corticosteroids, vitamin D analogues, and the combined agents. With the advent of topical treatments in tailored vehicles and sophisticated modes of delivery, the prospects for effective management of psoriasis with topical approaches appear promising. To ensure therapeutic success, patient education about disease, treatment options, administration and adverse effects is essential, which will alleviate the common problem of poor adherence of patients and promote optimal clinical outcomes (Kurian & Barankin, 2011).

Co-Morbidities

Over the last decade, multiple studies have shown that there is not only an association between psoriasis, psoriatic arthritis, depression and substance abuse, but patients with psoriasis also have a higher incidence of obesity, diabetes, heart disease and stroke. Most troubling is that young patients with psoriasis, particularly those with more severe disease, have a higher risk of mortality, even when controlled, because of these factors. Systemic inflammation in psoriasis generates elevated C-reactive protein, homocysteine, and inflammatory cytokines such as TNF-α, IL-6, IL-17, IL-20, IL-22 and IL-23, which may contribute to morbidity and overall mortality in these patients (Farley & Menter, 2011).

As previously mentioned, tetracyclines should be avoided in patients with psoriasis and in healthy people with a genetic predisposition to this disease (family history, human leukocyte antigens B13, B17, B27) as it has been shown that the disease becomes more severe during therapy with these drugs (Tsankov et al., 1988).

Early anecdotal evidence that both smoking and drinking have an influence on psoriasis had been confirmed in more detailed epidemiological studies. However, there seems to be some geographical variation between populations and a clear gender bias. The possibility that simple lifestyle modifications can reduce the prevalence and severity of psoriasis offers a great potential complement for treatment in the future (Higgins, 2000.

Helix Aspersa Müller

The common garden snail *Helix aspersa* Müller, also known as *Cryptomphalus aspersus* is a gastropod mollusca of the order Pulmonata, terrestrial life. Other names used are *Cryptomphalus aspersus, Cornu aspersum* and *Cantareus aspersus*. It is one of several species of the genus *Helix*, very similar, and also denominated snails. To move itself it requires the secretion of a mucus or drool, which when solidified serves as a support that isolates it from the unfavorable environment (operculation). It is hermaphrodite, oviparous and has a calcareous shell coiled in a spiral. Snail drool suitable for cosmetic application is obtained from fasting snails, which have been subjected to a state of stress by safe stimulation (by radiation or mechanical stress). This stimulation does not alter the survival of the animal and can be repeated several times during its life cycle. The slime secreted before these external stimuli has the capacity to repair the skin of the snail and to protect it from the external aggressions. These properties can be extrapolated for the formulation and application of cosmetic preparations (Abad R, 1996).

Snail slime, particularly of the species *Cryptomphalus aspersus* or *Helix aspersa* Müller, is constituted mainly by the following active principles, considered the most relevant:

Allantoin (glyoxyl-diurea): It helps eliminate necrotic, non-viable tissues, replacing them with new tissues and is anti-irritant. It promotes and accelerates the processes of natural healing in the body. It has also been mentioned as a cell proliferator and epithelial stimulant and helps to clean and eliminate necrotic tissue, accelerating the growth of healthy new tissue (Sznitowska M & Janicki S, 1988). The FDA has not recognized allantoin as a wound-healing agent, but as a skin protector, classified within category I, safe and effective.

Glycolic acid (hydroxyacetic acid). It is a natural organic compound of small molecular chain, which allows it to penetrate the skin quickly to deep strata. This acid is widely used in dermatological treatments, mainly to fade in any section of skin, wrinkles, stretch marks, scars and acne. As it is an irritant, it is recommended to use it with plant extracts, collagen and vitamins that support cellular reconstruction (Denda S, 2010). The function of this compound is to decrease the thickness of the stratum corneum of the skin and to increase the thickness of the Malpighian layer. It is also an excellent exfoliator and helps other components to penetrate the skin more easily (Elson M L, 1993, Tribó et al, 2004).

Elastin: 70 kDa protein, present in all vertebrates, with structural functions that provides resistance and elasticity to the tissues. It has a great capacity of expansion, which allows, against a wound treatment, the cure by expansion of the regenerating tissues (Sage & Gray, 1977; Young G L & Jewell D, 2000).

Collagen: The molecule allows the replacement of denatured collagen and the production of metalloproteinase inhibitors (TIMP), which facilitates regulation between the synthesis and degradation of the components of the dermis. It improves the cellular cytoskeleton, since it induces the proliferation and activation of fibroblasts thanks to the beta-EGF activity. As a result, the production of hyaluronic acid, collagen and elastin fibers, and the deposition of fibronectin in the extracellular matrix increases, thus favoring dermal support (Young G L & Jewell D, 2000).

Finally, the natural antibiotics contained in snail slime are substances capable of acting against bacteria normally present in the skin, especially *Eschericia Coli, Staphylococcus aureus, Pseudomona Aeruginosa* and *Acne vulgaris*, protecting against infection. Together with these more relevant components, the presence of vitamins and antibiotics is estimated to allow a greater rate of skin regeneration, decreased inflammation, and an inhibition of the infective processes characteristic of skin lesions. In this regard, it is particularly noteworthy that the empirical evidence suggests that all the components of the snail slug, in particular, the Chilean species (*Helix aspersa* Müller) act synergistically, a relevant aspect to be analyzed within the present application.

DETAILED DESCRIPTION OF THE INVENTION

The applicant of the present invention has been dedicated for the past years to the development of products based on snail slime of domestic species. Its development has been eminently for cosmetic use, generating several products that include: hand, body and facial cream, shampoo, conditioning balm and bath soaps, all of them currently registered and in the market.

Considering that snail slime components possess the healing, regenerative and antiseptic properties, among others, the applicant thought of generating a product specifically formulated for the healing and regeneration of wounds and lesions derived from psoriasis.

The inventors of the present application initially evaluated the product in a dermocosmetic manner as part of the popular use that is being given to snail slime, clearly taking advantage of the extraordinary qualities that have been seen in some people with different skin conditions, particularly psoriasis (FIG. 2). The product has been used as a complement to psoriatic treatments and it has been observed that the formulation with snail slime under study not only serves as a palliative treatment, but also curative for psoriatic lesions. It is therefore surprisingly clear that snail slime has an activity, which excels the conventional treatments.

The present invention is further directed to the development of an application/device, from the developed product, which will be more efficient and effective than the current treatment, which is essentially palliative and curative. This treatment may, at best, stop the development of the psoriatic wounds. The use of the product that we will develop can also allow the desquamation of dead skin and regeneration of new skin due to the properties of its components.

The product can be administered or installed by the patient, meaning the patient does not need to be moved and therefore does not require biomedical human resources associated with the treatment of the disease. For this, the device has a monograph of use with the appropriate indications for its better effectiveness.

In summary, the product/composition to be developed is an application/device as a patch or band (FIG. 1), easy to use for both qualified personnel and the patient himself, and can be of variable size. Its use is complementary to any other treatment.

The previous investigation of the state of the art has concluded that there is no national or worldwide alternative to this product, so that this would be novel, inventive and certainly with clear industrial application, the three fundamental aspects for the acceptance of a patent. Both the formulation and the form of application are novel because in previous analyzes of our group it has been possible to observe a greater effectiveness of this form or device versus the cream or gel applied on the diseased or ulcerous skin, which undergoes chemical and photochemical transformations, or microbiological processes that diminish its effectiveness and time of therapeutic utility.

EXAMPLES

The examples set forth below are incorporated by way of illustration only in order to promote understanding of the specification and do not imply that they limit in any way the scope of the claims being sought.

Example 1: Formulation Example

A) Formulation of the lotion

| Components | % w/v |
|---|---|
| Water | 70.00 |
| Snail slime filtrate | 5.00 |
| Liquid Paraffin | 6.00 |
| Glycerin | 5.00 |
| Cetearyl alcohol (CETEARETH-20) | 3.00 |
| Polyisobutene hydrogenated | 3.00 |
| Dimethicone | 1.00 |
| *Calendula officinalis* extract | 3.00 |
| PEG-100 glyceryl stearate/stearate | 1.00 |
| Propylene Glycol | 0.56 |
| *Prunus Amygdalus dulcis* oil | 0.50 |
| Tocopheryl acetate | 0.50 |
| Triethanolamine | 0.30 |
| Diazolidinyl Urea | 0.30 |
| Methyl Paraben | 0.26 |
| Acrylates/C10-30 alkyl acrylate cross-polymer | 0.20 |
| Perfume | 0.20 |
| Hydantoin DMDM | 0.14 |
| Propylparaben | 0.03 |
| Iodopropynyl Butylcarbamate | 0.01 |

B) Formulation of Soap

| Components | % w/v |
|---|---|
| Water | 71.38 |
| Sodium lauryl sulfate | 10.00 |
| Snail slime filtrate | 5.00 |
| Nettle Extract | 5.00 |
| Cocoamido propyl betaine | 3.00 |
| Glycerin | 2.00 |
| Cocoamide DEA | 1.50 |
| Hydantoin DMDM | 0.60 |
| Sodium Chloride | 0.50 |
| Methylparaben | 0.20 |
| Propylparaben | 0.15 |
| PEG-150 Stearate | 0.10 |
| Perfume | 0.50 |
| Citric acid | 0.07 |

C) Formulation for Body Cream

| Component | % |
|---|---|
| Water | 73.50 |
| Snail secretion filtrate | 5.00 |
| Liquid Paraffin | 6.00 |
| Glycerin | 5.00 |
| Cetearyl alcohol (CETEARETH-20) | 3.00 |
| Polyisobutene hydrogenated | 3.00 |
| Dimethicone | 1.00 |
| PEG-100 glyceryl stearate/stearate | 1.00 |
| Propylene Glycol | 0.56 |
| Tocopheryl Acetate | 0.50 |
| Diazolidinyl Urea | 0.30 |
| Methylparaben | 0.26 |
| Acrylates/C10-30 alkyl acrylate cross-polymer | 0.20 |
| Perfume | 0.20 |
| Hidantine DMDM | 0.14 |
| Propylparaben | 0.03 |
| Iodopropynyl Butyl carbamate | 0.01 |
| Triethanolamine | 0.30 |

| D) Formulation for Shampoo | |
|---|---|
| Component | % w/v |
| i) Chamomile/honey | |
| Water | 65.00 |
| Sodium Lauryl Sulfate | 10.00 |
| Cocoamido Propyl Betaine | 7.00 |
| Chamomile extract | 5.00 |
| Snail secretion filtrate | 5.00 |
| Sodium cocoanphodipropionate | 3.00 |
| Cocoamide DEA | 2.00 |
| MEL | 1.00 |
| PEG-150 Stearate | 0.10 |
| Hydantoin DMDM | 0.60 |
| Methylparaben | 0.15 |
| Propylparaben | 0.05 |
| Citric Acid | 0.05 |
| Perfume | 0.50 |
| Dimethicone | 0.50 |
| ii) Nettle | |
| Water | 60.00 |
| Sodium Lauryl Sulfate | 10.00 |
| Cocoamido Propyl Betaine | 8.00 |
| Nettle Extract | 5.00 |
| Snail secretion filtrate | 5.00 |
| *Rosmarinus officinalis* extract | 5.00 |
| Sodium cocoanphodipropionate | 3.00 |
| cocoamide DEA | 2.00 |
| PEG-150 Stearate | 0.10 |
| Hydantoin DMDM | 0.60 |
| Methylparaben | 0.15 |
| Propylparaben | 0.10 |
| Citric Acid | 0.05 |
| Perfume | 0.50 |
| Dimethicone | 0.50 |

*pH 6-7

Example 2: Manufacture of the Gel Patch Formulation

For the manufacture of 15 to 20 gel patches the following procedure is performed:

50 grams of body cream are sterilized by autoclaving at 150° C., with a rise time of temperature, exposure time and cooling time (30 minutes), then 30 grams of sterilized *Helix aspersa* Muller snail slime are added, homogenizes with stirring, then 10 ml liquid petroleum jelly and 10 ml bi-distilled water are added to maintain moisture. It is homogenized and then the patches are soaked with the gelatinous formulation having a viscosity of between 500 and 1,000 Pa-s.

Example 3: Administration and Dosage

The product is applied as a lotion, cream, gel, shampoo or patch containing these formulations, directly on the wound as follows, in the following cases:

Head Psoriasis

The product MUCIDERM snail shampoo is applied to the hair of people suffering from psoriasis, as follows:

Case 1: mildly ill: apply 5 to 10 mL of the chamomile-honey shampoo and massage the hair with the tip of the fingers for one minute, let the hair stand for two minutes and then rinse with plenty of water. Then the conditioning balm is applied in the proper way; that is: Apply and massage the hair with the tip of the fingers for one minute let the hair rest for two minutes and then rinse with plenty of water.

Case 2: mildly ill or sicker: apply 5 to 10 mL of nettle shampoo and massage the hair with the tip of the fingers for one minute, let the hair rest for two minutes and then rinse with plenty of water. Then the conditioner is applied in the same way, that is: Apply and massage the hair with the tip of the fingers for one minute let the hair rest for two minutes and then rinse with plenty of water. Possible cases of allergy should change to chamomile-honey shampoo.

Skin Psoriasis

The product MUCIDERM snail soap, is applied in the body of people suffering from psoriasis, as follows:

Case 1: Mildly sick: apply the chamomile-honey soap on the affected area with a sponge for at least 3 minutes and then rinse with plenty of water. Then the body lotion/cream is applied to the affected area. It is recommended to do this procedure twice a day for at least 3 days.

Case 2: mildly ill or sicker: apply the nettle soap on the affected area with a sponge, at least 3 minutes and then rinse with plenty of water. Then the body lotion/cream is applied to the affected area. Possible cases of allergy, should be changed to chamomile-honey soap. It is recommended to do this toilet twice a day.

Case 3: Sick to severe: In patients with episodes of obvious and severely irritating psoriasis, the gel patch (FIG. 3) should be applied with nettle in the affected area at night and left until the following morning, then wash the area with plenty of water and apply the body lotion/cream with nettle in the affected area. This process should be performed for 7 to 10 days. Possible cases of allergy, should be changed to chamomile-honey soap.

Psoriasis on the Face

The MUCIDERM repair cream product (face) is applied to the face of people suffering from psoriasis, as follows:

Case 1: Slightly ill: apply a minimal amount of chamomile-honey soap with a sponge all over the face, then rinse with plenty of water and finally apply face cream all over the face. The procedure should be performed at least twice a day.

Case 2: mildly ill or sicker: apply a minimal amount of nettle soap with a sponge all over the face, then rinse with plenty of water and finally apply face cream all over the face. The procedure should be performed at least twice a day. If allergy occurs, chamomile-honey soap should be used.

Example 4: Application Example

A 25-year-old girl with concurrent episodes of severe psoriasis in the arm, with an elemental lesion, i.e. an erythematous papule or plaque of varying size and dark red tone, borders and scaly, with bleeding (Auspitz sign), that is, petechiae as a consequence of the vascular damage of the dermal papillae, by the detachment of the epidermis that covers them, was treated with the gel patch of Example 2 (FIG. 3) with nettle in the affected area. The treatment consisted of the nocturnal application until the next morning of the patch on the injury, washing later the zone with abundant water. This process was performed for 10 days, a procedure that completely reversed the episode of psoriasis in the arm (FIG. 2), with no hyperkeratosis of the epidermis not evidencing the elemental lesion. It was observed that the decrease of the cutaneous sign was produced along with the elimination of urine of more intense color.

REFERENCES

Figure 1:
FIG. 1: Photograph of *Helix aspersa* Müller snail strain
Figure 2:
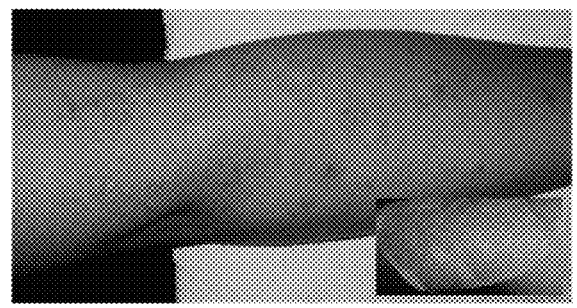
FIG. 2: Results of application of the patch-embedded product on arm skin with a seriologic episode. A) day 1 (box indicates mode of application of the patch), b) day 3, c) day 5, d) day 10.
Figure 2:
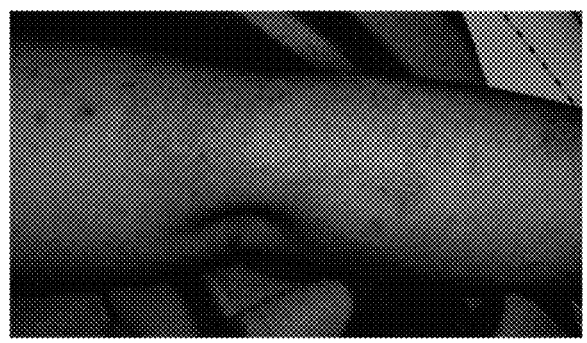
Figure 2:
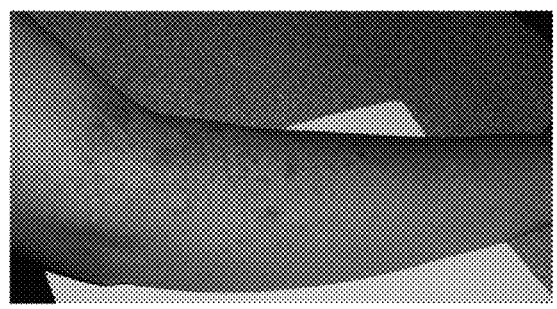
Figure 2:
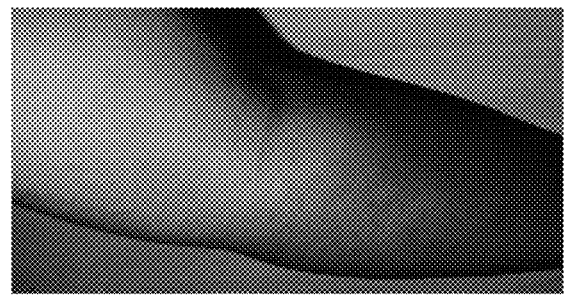
Figure 3:
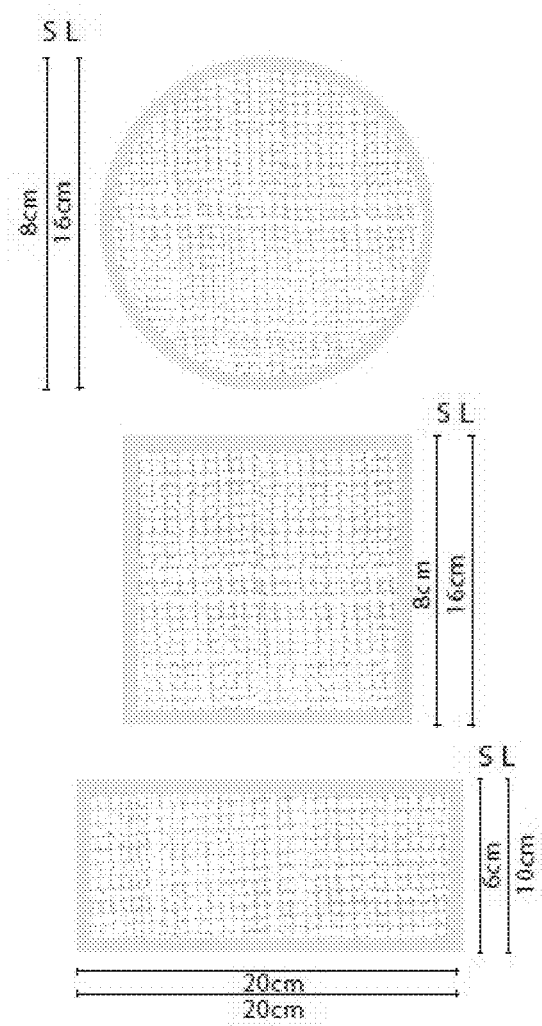
FIG. 3: Shape and dimensions of the various gauze patches or gel-embedded bandages of the invention for therapeutic purposes.

Abad R, Therapeutic and cosmetic compositions for treatment of skin, patente número 5538740, 1996.

Coto E, Santos-Juanes J, Coto-Segura P, Alvarez V. New soriasis susceptibility genes: momentum for skin-barrrier disruption. J Inves Dermatol. 2011 May: 131 (5): 1003-5.

De Korte J., Mombers F. M. C., Sprangers M. A. G. and J. D. Bos, The suitability of quality-of-life questionnaires for soriasis research: a systematic literature review, Arch Dermatol 138 (2002), pp. 1221-1227.

Denda S, Denda M, Inoue K, Hibino T. Glycolic acid induces keratinocyte proliferation in a skin equivalent model via TRPV1 activation. J DermatolSci. 2010 February; 57(2):108-13. Epub 2010 Jan. 8.

Elson M L. The molecular structure of glycolic acid and its importance in dermatology. Cosmetic Dermatology; 6(7): 35-40, 1993.

Farber E M. Studies on the nature and management of soriasis. Calif Med. 1971 June: 114 (6): 1-10.

Farley E, Menter A. *Soriasis: Comorbidities and associations*. G Ital Dermatol Venereol. 2011 February; 146(1): 9-15.

Gupta M. A., Gupta A. K. and S. Kirby, A psychocutaneous profile of soriasis patients who are stress reactors, Gen Hosp Psych 11(1989), pp. 166-173. Abstract.

Hayes J, Koo J. *Soriasis: depression, anxiety, smoking, and drinking habits*. Dermatol Ther. 2010 March; 23(2):174-80.

Higgins E., Alcohol, smoking and soriasis, Clin Exp Dermatol 25 (2000), pp. 107-110.

Kurian A, Barankin B. *Current effective topical therapies in the management of soriasis*. Skin Therapy Lett. 2011 January; 16(1):4-7. Review.

Rapp S. R., Feldmann S. R., Exum M. L., Fleischer A. B. and D. M. Reboussin, Soriasis causes as much disability as other major medical diseases, J Am Acad Dermatol 41 (1999), pp. 401-407.

Sage E H & Gray W R 1977 Evolution of elastin and elastin structure, p 291. in; Advances in Experimental Medicine and Biology, vol. 79 L B Sandberg & C Franzblaw, eds) Plenum Press, NY & London).

Sznitowska M, Janicki S. The effect of vehicle on allantoin penetration into human skin from an ointment for improving scar elasticity. Pharmazie. 1988 March; 43(3):218.

Tribó M J, Parrado C, Rais B et al. Preliminary results of the efficacy of intensive treatment with the secretion of *Cryptomphalus aspersa* (SCA) in phototherapy skin aging. Med CutanIberLat Am. 2004; 32:265-270.

Tsankov N, Botev-Zlatkov N, Lazarova A Z, Kostova M, Popova L, Tonev S. Soriasis and drugs: influence of tetracyclines on the course of soriasis. *J Am Acad Dermatol.* 1988 October; 19(4):629-32.

Tsankov N., Angelova I. and R. Kazandjieva, Drug-induced soriasis. Recognition and management, Am J Clin Dermatol 1(2000), pp. 159-165.

Turchin I, Adams S P. Demacase: soriasis. Can Fam Physician 52 (9): 1073, 1080 (2006 September).

Van de Kerkhof P C. *Options for the treatment of soriasis: a multifactorial approach*. Clin Dermatol. 2008 September-October; 26(5): 419-23.

Young G L, Jewell D. (2002). Creams for preventing stretch marks in pregnancy. Cochrane Database Syst Rev., (2): CD000066.

The invention claimed is:

1. A pharmaceutical composition for treating psoriasis lesions comprising:
   about 5% snail slime from *Helix aspersa* Muller; and
   about 5% weight/volume of nettle;
   wherein said snail slime and said nettle are dissolved in a base including one or more excipients, and said composition has a viscosity between 10-1000 Pa-s.

2. The composition of claim 1 wherein said viscosity is limited to 500 Pa-s.

3. The composition of claim 1 wherein said composition is in the form of a lotion.

4. The composition of claim 1 wherein said composition is in the form of a shampoo.

5. The composition of claim 1 wherein said composition is in the form of a soap.

6. The composition of claim 1 wherein said composition further comprising at least propolis.

7. The composition of claim 1 further comprising 5-10% chamomile extract.

8. The composition of claim 7 further comprising 5-10% honey.

* * * * *